US010175215B2

(12) United States Patent
Ozcan et al.

(10) Patent No.: US 10,175,215 B2
(45) Date of Patent: Jan. 8, 2019

(54) METHOD AND DEVICE FOR QUANTIFICATION OF PLANT CHLOROPHYLL CONTENT

(71) Applicant: THE REGENTS OF THE UNIVERSITY OF CALIFORNIA, Oakland, CA (US)

(72) Inventors: Aydogan Ozcan, Los Angeles, CA (US); Bingen Cortazar, Los Angeles, CA (US); Hatice Ceylan Koydemir, Los Angeles, CA (US); Derek Tseng, Buena Park, CA (US); Steve Feng, Danville, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 8 days.

(21) Appl. No.: 15/538,309

(22) PCT Filed: Dec. 21, 2015

(86) PCT No.: PCT/US2015/067103
§ 371 (c)(1),
(2) Date: Jun. 21, 2017

(87) PCT Pub. No.: WO2016/106215
PCT Pub. Date: Jun. 30, 2016

(65) Prior Publication Data
US 2018/0003686 A1 Jan. 4, 2018

Related U.S. Application Data

(60) Provisional application No. 62/096,345, filed on Dec. 23, 2014.

(51) Int. Cl.
*G01N 21/25* (2006.01)
*G01N 33/00* (2006.01)
(Continued)

(52) U.S. Cl.
CPC ....... *G01N 33/0098* (2013.01); *G01N 21/274* (2013.01); *G01N 21/31* (2013.01);
(Continued)

(58) Field of Classification Search
CPC ........ G01N 21/31; G01N 21/84; G01N 21/27; G01N 21/01; G01N 33/00; G06K 9/00;
(Continued)

(56) References Cited

U.S. PATENT DOCUMENTS

| 5,859,435 A | 1/1999 | Satake et al. | |
|---|---|---|---|
| 6,208,420 B1 * | 3/2001 | Satake | G01N 21/3563 250/339.07 |

(Continued)

FOREIGN PATENT DOCUMENTS

| JP | 10096692 A | 4/1998 |
|---|---|---|
| JP | 2011-038879 A | 2/2011 |

OTHER PUBLICATIONS

PCT International Search Report for PCT/US2015/067103, Applicant: The Regents of the University of California, Form PCT/ISA/210 and 220, dated Mar. 21, 2016 (3pages).
(Continued)

*Primary Examiner* — Abdullahi Nur
(74) *Attorney, Agent, or Firm* — Vista IP Law Group LLP

(57) ABSTRACT

A system for measuring chlorophyll concentration in a leaf sample includes a leaf-holding illuminator device with a main body containing a power source, a plurality of switchable light sources emitting light at different spectra (e.g., red and white light from a broadband light source), and a cap detachably secured to the main body using one or more fastening means. The leaf sample is interposed between the main body and the cap and held in place during imaging. The system includes a mobile electronic device having a camera configured to capture an image of the leaf illuminated by the
(Continued)

plurality of switchable light sources, the mobile electronic device having wireless connectivity to a network and an application contained therein configured to transfer the images to a remote sever or computer via the network for data processing. A final chlorophyll index value is calculated based on the transferred images.

20 Claims, 9 Drawing Sheets

(51) Int. Cl.
| | |
|---|---|
| *H04Q 9/00* | (2006.01) |
| *G01N 21/27* | (2006.01) |
| *G01N 21/31* | (2006.01) |
| *G06T 7/90* | (2017.01) |
| *G06K 9/00* | (2006.01) |
| *G06K 9/46* | (2006.01) |
| *G06K 9/62* | (2006.01) |
| *G01N 21/84* | (2006.01) |
| *G01N 21/01* | (2006.01) |
| *G06K 9/20* | (2006.01) |
| *G06K 9/22* | (2006.01) |

(52) U.S. Cl.
CPC ......... *G01N 21/84* (2013.01); *G06K 9/00657* (2013.01); *G06K 9/2054* (2013.01); *G06K 9/4661* (2013.01); *G06K 9/6202* (2013.01); *G06T 7/90* (2017.01); *H04Q 9/00* (2013.01); *G01N 2021/0125* (2013.01); *G01N 2021/8466* (2013.01); *G01N 2201/0221* (2013.01); *G01N 2201/0627* (2013.01); *G01N 2201/0634* (2013.01); *G06K 9/2027* (2013.01); *G06K 9/22* (2013.01)

(58) Field of Classification Search
CPC .. G06K 9/46; G06K 9/20; G06K 9/62; G06K 9/22
See application file for complete search history.

(56) References Cited

U.S. PATENT DOCUMENTS

| | | |
|---|---|---|
| 7,746,452 B2 | 6/2010 | Fuchigami et al. |
| 2010/0111369 A1 | 5/2010 | Lussier |
| 2014/0343863 A1 | 11/2014 | Imanishi et al. |

OTHER PUBLICATIONS

PCT Written Opinion of the International Search Authority for PCT/US2015/067103, Applicant: The Regents of the University of California, Form PCT/ISA/237, dated Mar. 21, 2016 (10pages).

CCM-200 plus Chlorophyll Content Meter, Opti-Sciences, Inc., www.optisci.com, 2005 (2pages).

SPAD 502 Plus Chlorophyll Meter, Product Manual, Item #2900P, 2900PDL, Spectrum Technologies, Inc., www.specmeters.com, 2009 (24pages).

Basyouni, Rania et al., Use of Optical Sensors to Monitor Plant Nitrogen Status in Horticultural Plants, Division of Agricultural Sciences and Natural Resources, Oklahoma University, HLA-6719-HLA-6719-4 , 2010 (4pages).

Li, Lei et al., A Review of Imaging Techniques for Plant Phenotyping, Sensors 2014, 14, 20078-20111; doi:10.3390/s141120078.

Liu, Bo et al., Plant Leaf Chlorophyll Content Retrieval Based on a Field Imaging Spectroscopy System, Sensors 2014, 14, 19910-19925; doi:10.3390/s141019910.

Richardson, Andrew D. et al., An evaluation of noninvasive methods to estimate foliar chlorophyll content, New Phytologis (2002) 153: 185-194, www.newphytologist.com.

PCT International Preliminary Report on Patentability (Chapter I of the Patent Cooperation Treaty) for PCT/US2015/067103, Applicant: The Regents of the University of California, Form PCT/IB/326 and 373, dated Jul. 6, 2017 (12pages).

\* cited by examiner

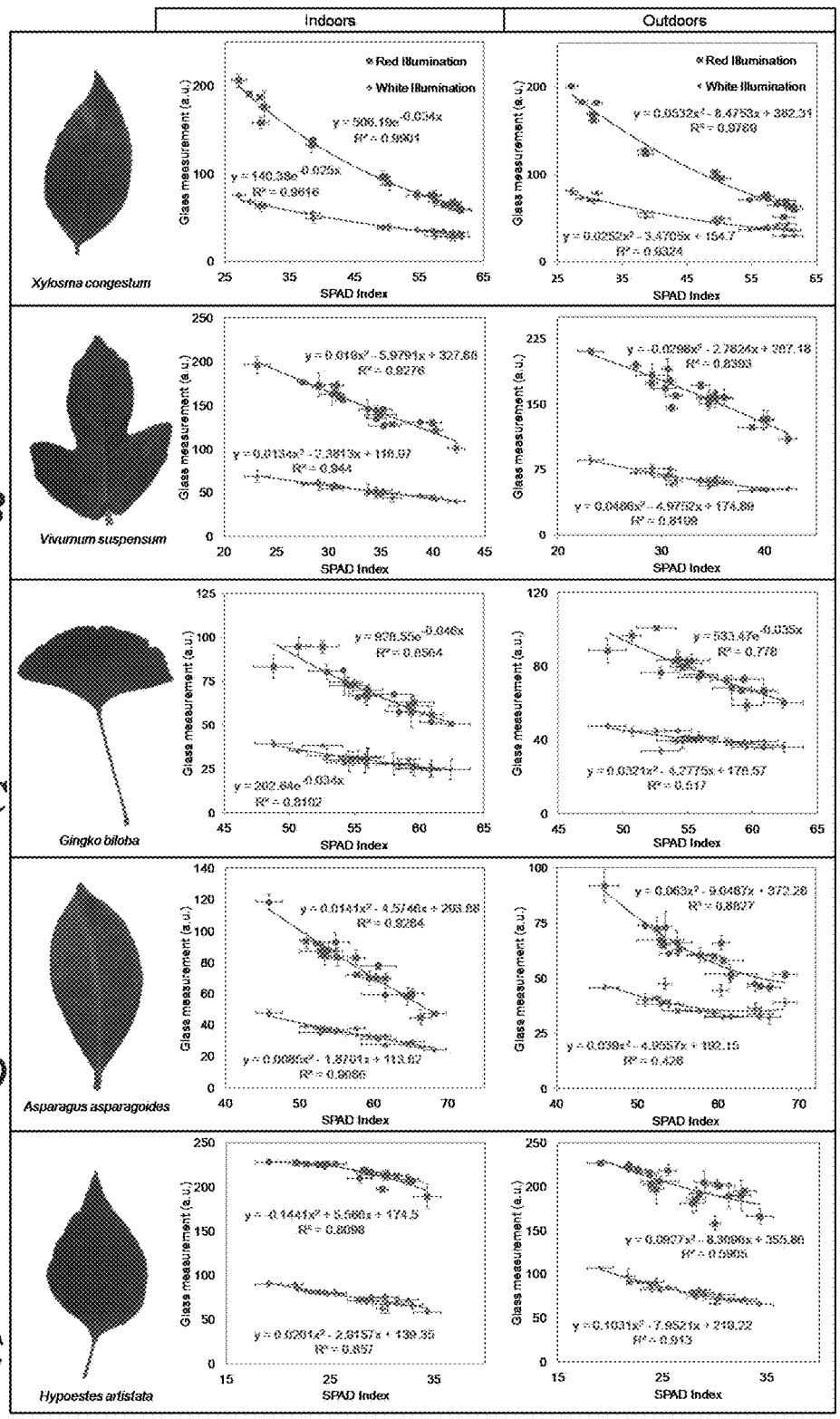

METHOD AND DEVICE FOR QUANTIFICATION OF PLANT CHLOROPHYLL CONTENT

RELATED APPLICATION

This Application is a U.S. National Stage filing under 35 U.S.C. § 371 of International Application No. PCT/US2015/067103, filed Dec. 21, 2015, which claims priority to U.S. Provisional Patent Application No. 62/096,345 filed on Dec. 23, 2014. Priority is claimed pursuant to 35 U.S.C. § 119 and any other applicable statute. The above-noted Patent Applications are incorporated by reference as if set forth fully herein.

STATEMENT REGARDING FEDERALLY SPONSORED RESEARCH OR DEVELOPMENT

This invention was made with Government support under 0954482 awarded by the National Science Foundation. The Government has certain rights in the invention.

FIELD OF THE INVENTION

The technical field generally relates methods and devices used to measure chlorophyll concentration in plant leaves.

BACKGROUND OF THE INVENTION

Large-scale industrialization over the past century has led to a variety of expanding environmental impacts (e.g., air, soil and water pollution, deforestation, desertification), resulting in both urban and rural public health safety concerns and significant concern over human-driven planetary changes. Changes in climate include changes in precipitation distribution and an increase in average temperatures globally, significantly impacting plant and animal ecosystems in various ways such as e.g., plant growth rates, soil mineralization, metabolic rates, life-cycle changes and animal migration patterns. Due to their ubiquitous and resilient nature, plant health and growth rates have been used as indicators for various environmental factors. For agriculture applications, rapid plant monitoring has remained a subject of great importance for maintaining plant health and identifying potential emerging diseases, which can affect plant storage dynamics and crop production efficiency.

Mainstream efforts have focused on indirectly measuring plant chlorophyll concentration, which is considered an important metric for general plant health. Abnormal levels of chlorophyll may be indicators of important plant stress agents such as e.g., plant diseases, environmental stress, lack of or excess amounts of nutrients, light, or water, or the presence of toxic substances (e.g., cadmium). Currently, the "gold" standard for direct measurement of plant chlorophyll concentration is through chemical extraction of the chlorophyll from plant specimens, whereby plant leaves are mechanically dissociated and dissolved using chemicals (e.g., acetone). The chlorophyll is then filtered from the other plant compounds and pigments and chlorophyll levels are subsequently measured using a spectrophotometer. This process is inherently destructive, expensive, complex, and, due to its sample preparation steps requires trained personnel within a controlled lab environment (and proper equipment). To combat these disadvantages, over the past three decades several indirect methods for estimating chlorophyll levels of plants have been developed. Hyperspectral satellite imaging techniques using indirect chlorophyll estimation systems have been effectively used to control and monitor crop fields and forested regions, deforestation processes, and the spread of invasive species. While effective at the macro scale, these methods require complex and expensive hardware and time-consuming data acquisition and processing. In recent years, various hand-held optical systems (e.g. GreenSeeker™, atLeaf+, or SPAD 502Plus) have also been developed to form portable instruments for estimating the chlorophyll information of plants in a local region. One of the most reliable and most frequently used hand-held device is the commercially available SPAD-502Plus (Special Product Analysis Division) chlorophyll meter offered by Spectrum Technologies, Inc., which uses ratio-metric analysis of the light absorption of a leaf under a red LED (peak wavelength of 650 nm) and an infrared LED (peak wavelength of 940 nm) for estimation of site-specific chlorophyll concentration levels on the leaf. While widely used for agriculture and plant physiology studies, this device is relatively expensive and only provides an estimation of chlorophyll levels for a small (2 mm×3 mm) area on the leaf surface, necessitating multiple measurements across other areas of the leaf surface for estimation of the overall leaf chlorophyll concentration. There is a need for other hand-held devices and systems that can effectively measure chlorophyll levels in plant leaves.

SUMMARY

In one aspect of the invention, a small, cost-effective leaf holder device having a multi-spectral illuminator therein is paired (e.g., used) with a mobile electronic device having camera functionality and wireless connectivity as part of a system that is used to measure chlorophyll levels in plant leaves. The mobile electronic device has a program or application that is stored therein that is able to acquire images of an illuminated leaf contained in the leaf holder device at multiple illumination wavelengths or spectra and then transmit these images to a remote computer (e.g., remote server or the like). In one preferred aspect of the invention, the leaf is illuminated with red illumination (e.g., from a red LED) and separately with white illumination (e.g., from a white LED). The images that are acquired and transmitted are then processed to identify a region of interest (ROI) in each image. After identifying the ROI in the images, the red color channel of the images is extracted for each image. Each image is then scored or given a value representative of the average value of all of the non-zero intensity values of the ROI. For example, in the red/white illumination scheme discussed above, there is an average intensity value for the ROI that was obtained from white light source $ROI_{white}$ and an average intensity value for the ROI that was obtained from red light source the $ROI_{red}$. These two average intensity values are then correlated with a calibration curve or equivalent to generate an index value. In one embodiment, the index value that is generated is a SPAD index which corresponds to a commonly used index that is generated, for example, with the SPAD 502Plus device. Of course, the calibration curves or their equivalent may be used to generate other indices commonly used to measure chlorophyll content. Another example includes, for example, the chlorophyll content index (CCI).

After the index has been generated, the calculated index value may be returned to the mobile electronic device (or, alternatively the final index may be calculated locally in the mobile electronic device). The calculated index along with other information (e.g., image, text, gps coordinates, species, details of calibration graph, etc.) may be presented to the user on the mobile electronic device. In one aspect of the invention, the mobile electronic device is a wearable imaging device (e.g., glasses-based imaging device) although the invention is not so limited. The mobile electronic device may also be a mobile phone (e.g., smartphone), tablet-based device, or webcam.

In one embodiment, a device for the measurement of chlorophyll concentration in a leaf includes a leaf-holding illuminator device. The leaf-holding illuminator includes a power source (e.g., batteries) and two switchable light sources (red and white). Power is regulated through a voltage regulator. The electronic components are contained within a main body or housing of the leaf-holding illuminator device that protects the electronics and forms a uniform light pattern internally. The device includes an external light isolation cap that is added to reduce light changes on the internally illuminated leaf area. The leaf is placed between the main body or housing and the cap with the cap being held to the main body using magnets or other fasteners for easy attachment/detachment. Illumination light from the two light sources is directed at the leaf. The illumination light may be direct or, alternatively, reflected off a reflecting surface containing the main body. Prior to light reaching the leaf surface, the light passes through a diffuser in order to generate a uniform illumination pattern on the leaf surface. In some embodiments, the light is transmitted through the leaf (i.e., transmission mode) while in other embodiments, the light is reflected off of the leaf (i.e., reflection mode).

The system or platform includes a mobile electronic device that, in one aspect of the invention, is a wearable imaging device such as Google Glass. The Google Glass device, which is worn by a user, includes an application or software program that is designed to capture images of the illuminated leaf from the leaf-holding illuminator device. Images are taken of the leaf in both red light and white light. These images are then uploaded to a remote server using Google Glass's wireless connection (e.g., WiFi) functionality. At the remote server, the images are digitally processed (e.g., cropped) to identify a ROI. The red channel of the ROI (for the red light illuminated and white light illuminated images) is then extracted and the average intensity level is obtained for each ROI. A calibration curve is used to convert the average intensity values (white and red) to index values (e.g., SPAD values) that correspond to chlorophyll concentration. The two index values are averaged and returned to the user by the remote server. As noted, the calculated chlorophyll concentration may be in the form of a SPAD index. Additional information that may be returned include image of ROI, date and time of image capture, validity of ROI region, GPS coordinates, and the like.

In one embodiment, a system for measuring chlorophyll concentration in a leaf sample includes a leaf-holding illuminator device comprising a main body containing a power source, a plurality of switchable light sources emitting light at different spectra, a diffuser interposed within an optical path formed between the plurality of switchable light sources and the leaf, and a cap having an aperture therein that is detachably secured to the main body, wherein the leaf sample is interposed between the main body and the cap. The cap may be secured to the main body using a number of different fastening methods. The system includes a mobile electronic device having a camera configured to capture images of the leaf illuminated by the plurality of switchable light sources, the mobile electronic device having wireless connectivity to a network and an application contained therein configured to transfer the images to a remote computer via the network as well as receive data from the remote computer (e.g., results or calculated index values).

The remote computer, which may include a server, performs data processing on the images. This includes cropping the ROI in the images and extracting the red channel intensity measurements for the cropped ROIs (average intensity values). The average intensity values are then compared with corresponding calibration curves or functions (or their equivalent) to generate a SPAD index value. The SPAD index values from the different illumination wavelengths (e.g., using two different lasers or light emitting diodes) are averaged to produce a final SPAD index value according to one embodiment. In other embodiments, different functions may be used to determine a final index value based on index value for each database. The remote computer returns this final SPAD index value back to the mobile electronic device. In an alternative embodiment, the final SPAD index value is calculated at the mobile electronic device instead of the remote computer.

In another embodiment, a leaf-holding illuminator device is disclosed that includes a main body having an interior cavity and a leaf-supporting surface. A power source is disposed on or in the main body portion. A plurality of light sources emitting light at different spectra are disposed in the interior cavity. A switch is located on the device and connects the plurality of light sources to the power source. The device includes a cap comprising a base having an aperture therein and an extension extending from the base at the aperture, the cap detachably secured to the leaf-supporting surface of the main body, wherein the leaf is held in place between the main body and the cap. The cap and main body may be secured together using any number of fasteners.

In another embodiment, a method of measuring chlorophyll concentration in a leaf sample includes the operations of loading the leaf sample into a leaf-holding illuminator device and illuminating the leaf sample with a leaf-holding illuminator device at a first illumination spectrum with a first illumination source and a second illumination spectrum with a second illumination source. Images of the illuminated leaf sample are captured with a camera of a mobile electronic device while being illuminated at the first illumination spectrum and the second illumination spectrum. The mobile electronic device transfers the captured images at the first illumination spectrum and the second illumination spectrum to a remote server. The remote server extracts a region of interest (ROI) from each of the transferred images and computes an average intensity value for the ROI obtained by the first illumination source and an average intensity value for the ROI obtained by the second illumination source. The remote server generates a chlorophyll index value for the first illumination source based on a comparison of the average intensity value for ROI obtained by the first illumination source with a calibration curve and also generates a chlorophyll index value for the second illumination source based on a comparison of the average intensity value for ROI obtained by the second illumination source with a calibration curve. The remote server calculates a final chlorophyll index value based on the chlorophyll index value for the first illumination source and the chlorophyll index value for the second illumination source and transfers the final chlorophyll index value to the mobile electronic device.

In another embodiment, a method of measuring chlorophyll concentration in a leaf sample includes the operations of loading the leaf sample into a leaf-holding illuminator device and illuminating the leaf sample with a leaf-holding illuminator device at a first illumination spectrum with a first illumination source and a second illumination spectrum with a second illumination source. Images of the illuminated leaf sample are captured with a camera of a mobile electronic device while being illuminated at the first illumination spectrum and the second illumination spectrum. The mobile electronic device transfers the captured images at the first illumination spectrum and the second illumination spectrum to a remote server. The remote server extracts a region of interest (ROI) from each of the transferred images and computes an average intensity value for the ROI obtained by the first illumination source and an average intensity value for the ROI obtained by the second illumination source. The remote server generates a chlorophyll index value for the first illumination source based on a comparison of the average intensity value for ROI obtained by the first illumination source with a calibration curve and also generates a chlorophyll index value for the second illumination source based on a comparison of the average intensity value for ROI obtained by the second illumination source with a calibration curve. The remote server transfers the chlorophyll index value for the first illumination source and the chlorophyll index value for the second illumination source to the mobile electronic device and the mobile electronic device calculates a final chlorophyll index value based on the chlorophyll index value for the first illumination source and the chlorophyll index value for the second illumination source.

Experiments were conducted on leaves using a hand-held leaf holder with two-color illumination (red/white) which was paired with Google Glass, a cloud-connected wearable computer integrated with a camera and various spatio-temporal sensors. Utilizing Google Glass running a custom-developed Android application, a rapid, accurate and non-destructive leaf chlorophyll measurement platform was demonstrated. The hand-held leaf holder external device was compared against the SPAD-502 Plus meter using its standard SPAD chlorophyll index value, which directly maps to chlorophyll levels in plants. Using different plant species across a range of SPAD indices, the Google Glass based chlorophyll estimator was used to generate calibration curves (for indoor and outdoor conditions, separately) matching the sensitivity of a commercial SPAD-502 meter. After this calibration step, the same system was used to accurately estimate (blindly) the chlorophyll indices of fifteen different plant species, selected from the UCLA Mildred E. Mathias Botanical Garden, under both indoor and outdoor lighting conditions. The Google Glass based rapid and non-destructive chlorophyll measurement platform can prove useful for urban plant monitoring, indirectly measuring the effects of climate change, as well as for early detection of water, soil, and air quality degradation.

BRIEF DESCRIPTION OF THE DRAWINGS

FIG. 4A illustrates measurements and calibration curves for the plant species *Xylosma congestum* obtained with the glasses-based imaging device that map intensity to SPAD index for both indoor and outdoor light conditions. Curves for both red illumination and white illumination are shown.

FIG. 4B illustrates measurements and calibration curves for the plant species *Vivurnum suspensum* obtained with the glasses-based imaging device that map intensity to SPAD index for both indoor and outdoor light conditions. Curves for both red illumination and white illumination are shown.

FIG. 4C illustrates measurements and calibration curves for the plant species *Gingko biloba* obtained with the glasses-based imaging device that map intensity to SPAD index for both indoor and outdoor light conditions. Curves for both red illumination and white illumination are shown.

FIG. 4D illustrates measurements and calibration curves for the plant species *Asparagus asparagoides* obtained with the glasses-based imaging device that map intensity to SPAD index for both indoor and outdoor light conditions. Curves for both red illumination and white illumination are shown.

FIG. 4E illustrates measurements and calibration curves for the plant species *Hypoestes artistata* obtained with the glasses-based imaging device that map intensity to SPAD index for both indoor and outdoor light conditions. Curves for both red illumination and white illumination are shown.

DETAILED DESCRIPTION OF THE ILLUSTRATED EMBODIMENTS

Figure 1A:
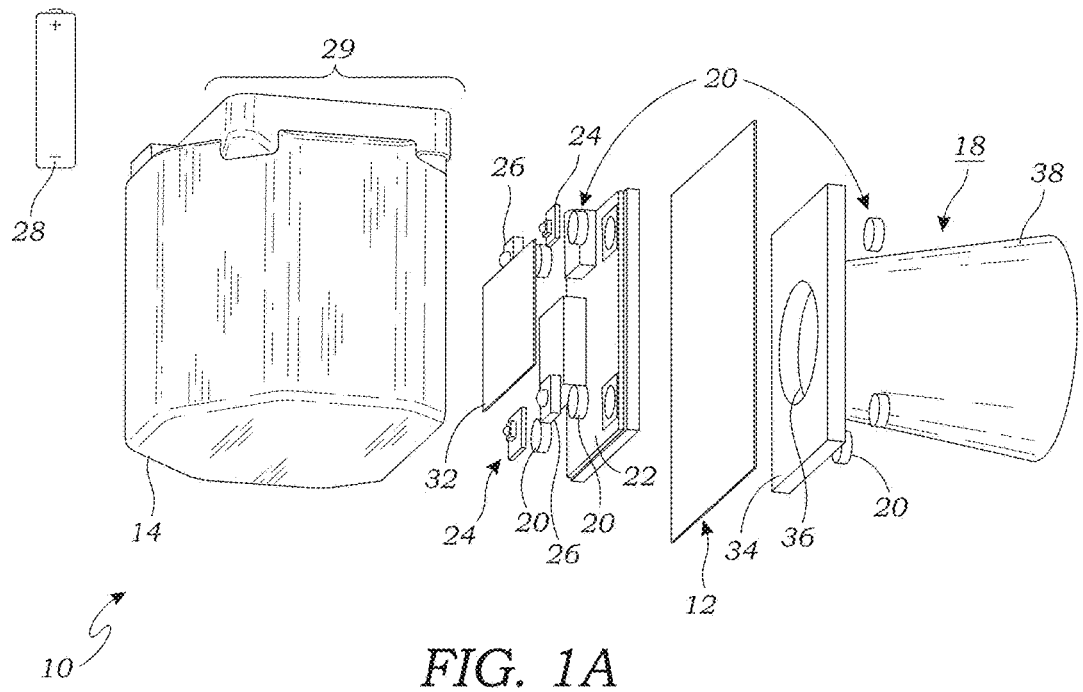
FIG. 1A illustrates an exploded view of a leaf-holding illuminator device according to one embodiment.
Figure 1B:
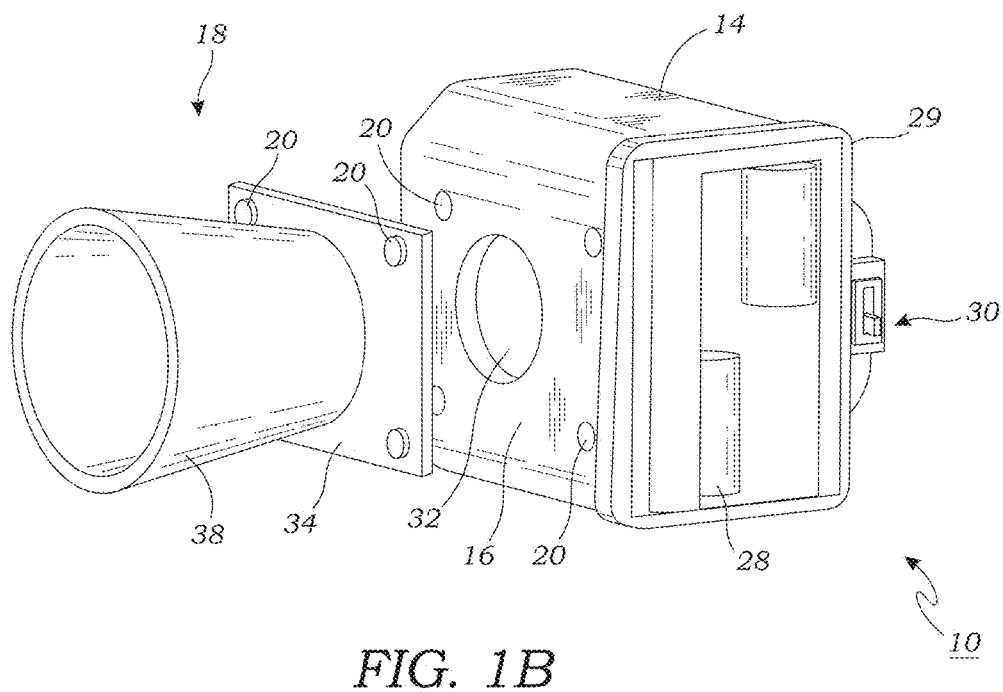
FIG. 1B illustrates a perspective view of the leaf-holding device illustrating the cap separated from the main body. The battery cover is removed illustrating the batteries contained therein.

FIGS. 1A and 1B illustrate an embodiment of a system for measuring chlorophyll concentration in a leaf sample according to one embodiment. Chlorophyll concentration is measured, as explained below, by returning a chlorophyll index value that is used as proxy or indicator of chlorophyll concentration. This may include a chlorophyll content index (CCI) or a SPAD index value. The system includes a leaf-holding illuminator device 10 that is used to hold a leaf 12 therein and illuminates the leaf 12 sequentially with different illumination spectra from separate illumination sources (e.g., LEDs or lasers). As explained below, the transmitted light through the leaf 12 at each emitted spectra is captured using a mobile electronic device 50 that includes a camera 64 therein. The leaf-holding illuminator device 10 includes a main body 14 or housing with leaf-supporting surface 16 that holds the leaf 12 and is covered with a removable cap 18. The leaf-supporting surface 16 includes an aperture therein so that light may pass from the main body 14 and through the leaf 12 (in transmission mode). The aperture may be open as illustrated or an optically transparent window can be formed in the leaf-supporting surface 16. During use, the leaf 12 is interposed between the leaf-supporting surface 16 of the main body 14 and the removable cap 18 in a sandwich-type arrangement. In one embodiment, the main body 14 and the removable cap 18 each include one or more magnetic elements 20 (e.g., a permanent magnet or magnetically susceptible material) mounted about the periphery of the main body 14 and/or removable cap 18 in corresponding locations such that magnetic attraction holds the cap 18 securely against the main body 14 with the leaf 12 pinched between the two components.

As an alternative to magnetic elements 20 various other mechanical attachment schemes could be used to secure the removable cap 18 to the main body 14. For example, clasps, clips, tabs, or latches could be employed to secure the two components together. One or more fasteners could also be used for this same purpose (e.g., screws, bolts, nuts, and the like) to secure these two components together. An elastic band or something similar could also be employed to secure the two pieces together as well. The two pieces might also be secured to one another using a friction fit between the removable cap 18 and the main body 14. For example, the cap 18 may have edges that fit within slots or the like formed in the main body 14 (or vice versa). These alternative mechanical attachment schemes are referred to herein as fastening means.

The main body 14 or housing may be made from an optically opaque plastic or polymer material. The main body 14 or housing includes an interior portion that houses an electronic circuit board 22 that contains the electronics for the leaf-holding illuminator device 10. This includes a first light source 24 and a second light source 26 with each respective light source 24, 26 emitting light or illumination at different spectra. Note that there may be some overlap in the spectra emitted by each light source 24, 26. For example, the first light source 24 and the second light source 26 may include one or more light emitting diodes (LEDs). In one aspect of the invention, the first light source 24 includes two red colored LEDs (645 nm peak wavelength) and the second light source 26 includes two white colored (i.e., broadband) LEDs. The first light source 24 and the second light source 26 are connected to a power source 28 such as batteries, (e.g., three alkaline batteries) which are stored in a battery compartment 29 on or within the main body 14, via a switch 30 located on the main body 14 that is selectively switched to turn on either the first light source 24 or the second light source 26 (or both off). A voltage regulator (not shown) is used to regulate power to the first and second light sources 24, 26 and is located on the electronic board 22.

Referring to FIG. 1A, light emitted from the first light source 24 and the second light source 26 are first passed through an optical diffuser 32 to provide for uniform lighting of the leaf 12. In one embodiment, as illustrated in FIG. 1A, the first light source 24 and the second light source 26 are arranged in a reverse orientation whereby the respective light sources 24, 26 transmit light into the interior cavity of the main body 14 which is then reflected back in the opposite direction using a reflective surface (not shown) disposed in the main body 14 or on an interior surface thereof. This may include a reflective foil or such as aluminum or a mirrored surface. In this regard, an optical path is created that passes from the respective light sources 24, 26, through the optical diffuser 32, onto the reflective surface, and back towards the direction of the leaf 12 that is sandwiched between the main body 14 and the cap 18. Alternatively, the optical diffuser 32 may be used after the light has reflected off the reflective surface. In still another alternative embodiment, the respective light sources 24, 26 can be oriented in a forward direction to directly illuminate the leaf 12 after passing through an optical path from between the respective light sources 24, 26, the optical diffuser 32, and the leaf 12. In these modes, the leaf-holding illuminator device 10 operates in a transmission mode whereby light passes through the leaf 12 and is imaged.

In yet another alternative embodiment, the leaf-holding illuminator device 10 may operate in a reflection mode whereby light that is reflected off of the surface of the leaf 12 is imaged. In this embodiment, the light sources 24, 26 illuminate a surface of the leaf 12 using, for example, an optical diffuser 32, and the reflected light from the surface of the leaf 12 is imaged. The spectra of the light sources 24, 26 may change depending on whether the leaf-holding illuminator device 10 operates in the transmission mode or the reflection mode. In either mode, however, a portion of the illuminated surface of the leaf 12 is imaged.

As seen in FIGS. 1A and 1B, the cap 18 includes a base portion 34 that includes an aperture 36 therein. The aperture 36 is circular-shaped although other shapes could be used. A frustoconical-shaped extension 38 extends from the base portion 34 and surrounds the aperture 36. The extension 38 reduces intensity changes on the internally illuminated area of the leaf 12 due to external lighting conditions (e.g., it prevents external light from interfering with the process of obtaining an image of light transmitted through the leaf 12). The leaf 12 can be placed into position without inflicting any damage to the leaf 12 by first removing the cap 18 and placing the leaf 12 on the main body 14 and then placing the cap 18 over the leaf 12 which then secures to the main body 14 via magnetic elements 20.

During use, a user places the leaf 12 between the cap 18 and the main body 14 as illustrated above. The leaf-holding illuminator device 10 is used in conjunction with a mobile electronic device 50 that has a camera therein. The mobile electronic device 50 may include, for example, a wearable mobile electronic device 50 such as a glasses-based device such as Google Glass (made by Alphabet, Inc.) with imaging functionality although other "wearables" may also be used such as headsets, etc. Alternatively, the mobile electronic device 50 may include a mobile phone such as Smartphones or the like that include a camera 64 therein such as the Smartphone illustrated in FIG. 1C. The mobile electronic device 50 may also include tablet, tablet PC, or other similar devices with camera functionality (e.g., webcam).

Figure 1C:
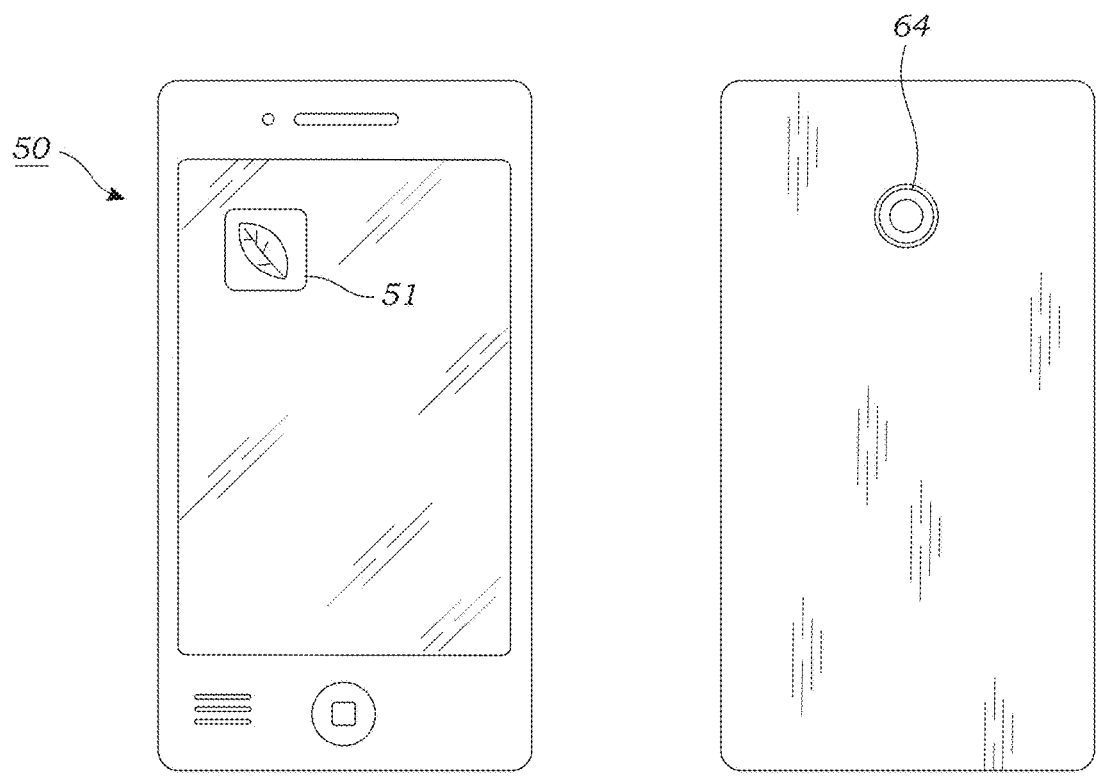
FIG. 1C illustrates front and back views of a mobile electronic device (e.g., Smartphone) having camera functionality that is used with the leaf-holding illuminator device.
Figure 2:
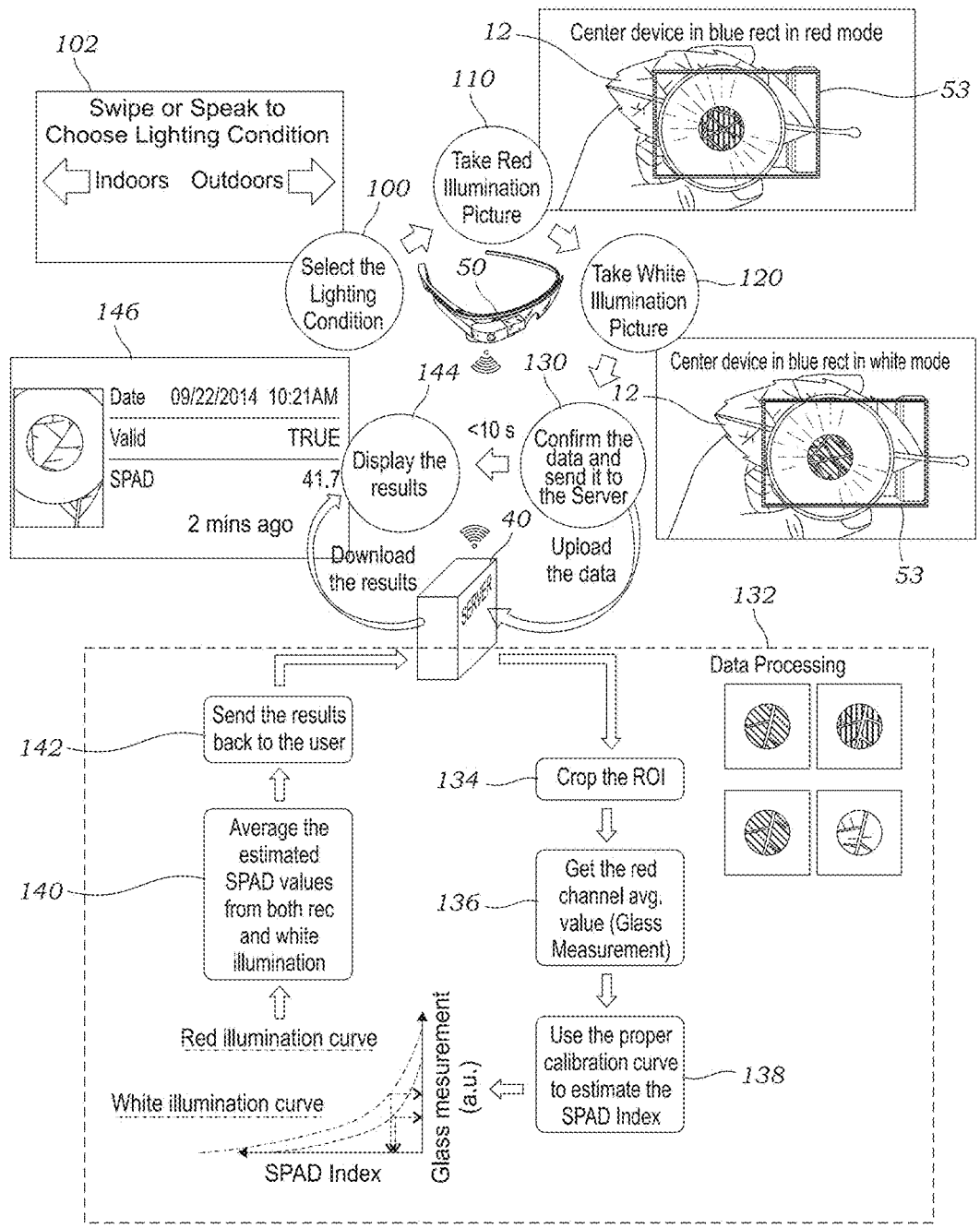
FIG. 2 illustrates an illustrative process for measuring chlorophyll concentration in a leaf sample using the leaf-holding illuminator device and the mobile electronic device with camera functionality.

The mobile electronic device 50 includes a program or application 51 (e.g., "app") that runs on the mobile electronic device 50. The program or application may run on any number of operating systems although the specific example described herein is run using the Android operating system. FIG. 1C illustrates an icon for the application 51 on a display of the mobile electronic device 50 that can be executed by touching the same. FIG. 2 illustrates the typical operations used to measure the chlorophyll content in a leaf 12 according to one embodiment of the invention. First, the leaf 12 is loaded into the leaf-holding illuminator device 10. The user initiates the application or program 51 on the mobile electronic device 50 to begin the chlorophyll measurement. Initially, as seen in operation 100, the user is asked by the application 51 to select the lighting condition which in this example is whether the image is taken indoors or outdoors. Other lighting conditions beyond these two specific lighting conditions may also be used (e.g., bright sunlight, dusk, overcast, etc.). For example, as seen in exemplary screen shot 102 as user can swipe right for outdoors or swipe left for indoors. Next, the user adjusts the switch 30 (FIGS. 1A and 1B) to turn on the red light source 24 on the leaf-holding illuminator device 10, although the red light source 24 could already be turned on when the user initiates the application in the mobile electronic device 50. In operation 110, the user obtains an image of the transmitted light through the leaf 12 using the red light source 24. The mobile electronic device 50 may prompt the user with text instructions such as "take a picture of the leaf with the red light." During this operation, the user may be presented with a template or overlay 53 on the screen, display, or graphical user interface on the mobile electronic device 50 which the user can use to aid in aligning or matching with the aperture 26. The template or overlay 53 may ensure that the proper distance and alignment is achieved prior to obtaining the image.

Next, in operation 120, the user obtains an image of the transmitted light through the leaf 12 using the white light source 26. The switch on the leaf-holding illuminator device 10 is switched to turn off the red light source 24 and turn on the white light source 26. The mobile electronic device 50 may prompt the user again with text instructions such as "take a picture of the leaf with the white light." The user again may be presented with a template or overlay 53 on the screen, display, or graphical user interface on the mobile electronic device 50 which the user can use to aid in aligning or matching with the aperture 26. After the image of the light using the white light source 26 has been obtained, the user confirms the data (e.g., responding to a question or statement on the mobile electronic device 50) and the images (obtained with the red and white illumination light) are transferred to a remote server 40 in operation 130. The images may be automatically compressed using a compression algorithm such as the well-known JPEG format. The images may be transmitted over a WiFi network connected to a wide area network such as the Internet or other network such as a mobile phone network. Note that in this embodiment, the system is arranged in a cloud-based environment whereby images are obtained locally and data processing occurs remotely or "in the cloud." The images are subject to data processing 132 in the remote server 40. In some alternative embodiments, some data processing 132 may take place locally on the mobile electronic device 50.

As seen in FIG. 2, data processing 132 first involves validating the images using a cropped ROI in operation 134. The ROI is digitally cropped using the template or target location (used to obtain the images) and the resulting cropped image is scanned for circular shapes with parameters corresponding to the aperture 36 of the cap 18. Of course, other shapes could be scanned depending on the geometric shape of the aperture 36. Upon successful detection of the circular aperture 36, the ROI is further limited by additional digital cropping to a 110 pixel radius circular ROI that includes a 40 pixel margin to avoid boarder or edge effects and enhance repeatability of the experiments.

After successful detection of the illuminated leaf ROI, the red channel information is extracted from both the red-illuminated and white-illuminated cropped ROI images as seen in operation 136. For each red channel image, the average intensity of all the non-zero pixels in the circular masked leaf ROI is then obtained. These two values, the average intensity value (a.u.) for the ROI that was obtained from white light source $ROI_{white}$ and an average intensity value (a.u.) for the ROI that was obtained from red light source the $ROI_{red}$ are then correlated with a calibration curve or equivalent (such as a look-up table, mapping function, or the like) to generate an index value that corresponds to the chlorophyll concentration as seen in operation 138. In one embodiment, the index value that is generated is a SPAD index which corresponds to a commonly used index that is generated, for example, with the SPAD 502Plus device. Another example includes, for example, the chlorophyll content index (CCI). The calibration curves or their equivalent are obtained by using experimentally obtained calibration curves for the different lighting conditions (e.g., outdoor or indoor). The calibration curves or their equivalent are stored in or otherwise accessible by the remote server 40 (e.g., stored in a file or database accessible by the remote server 40). The calibration curves or their equivalent may be specific to the species of the plant from which the leaf 12 was obtained. Alternatively, the calibration curves or their equivalent may be generic to a particular plant species. As noted herein, good results may be obtained with generic calibration curves.

Still referring to FIG. 2, a SPAD index value is obtained for the white illumination as well as the red illumination. To reduce variability caused by differing plant physiology and lighting conditions these two SPAD index values are then averaged to produce a final SPAD index for the leaf 12 as seen in operation 140. Finally, as seen in operation 142, the results are then sent or otherwise transferred back to the user. This transfer back to the user may occur automatically or the user may retrieve the results manually. Again, this transfer from the remote server 40 to the mobile electronic device 50 occurs over a network such as WiFi connected to the Internet or a mobile phone network. The transfer back to the mobile electronic device 50 may include direct data transfer from the remote server 40 to the program or application 51 on the mobile electronic device 50 or the transfer may be sent via e-mail or text message to the mobile electronic device 50.

As noted above, the final SPAD index for the leaf 12 was calculated at the remote server 40 and then transferred back to the application 51. Alternatively, the final SPAD index (or other final chlorophyll index level) may be calculated in the mobile electronic device 50 by the application 51 instead of the remote server 40. For example, the remote server 40 may transmit the red SPAD index value and the white SPAD index value to the mobile electronic device 50. The application 51 in the mobile electronic device 50 may then calculate the "final" SPAD index based on these transmitted values. For example, the application 51 running on the mobile electronic device 50 may calculate the average of the two index values.

In addition, FIG. 2 discusses an embodiment where the red SPAD index value is averaged with the white SPAD index value, it should be understood that there can be other functions besides taking an average of the two indices. In general, the function may be any arbitrary function for $f(x,y)$ where x and y are the respective average index values for each illumination source. Of course, the function would be chosen that is appropriate for the particular plant species. For example, one spectra color of the index value could be weighted over the other spectra or color. These different functions may be specific to a particular plant species. Again, these computations could be made at the remote server 40 or they could be made by the application 51 in the mobile electronic device 50.

As seen in operation 144, in one embodiment, the results are displayed to the user on the display associated with the mobile electronic device 50. The results that are displayed include the final index value (e.g., final SPAD index value) along with an image of the leaf ROI, text that may include test details such as date, time, gps coordinates, species, validation information, details of calibration graph, and the like as seen in screen shot 146. It should be understood that the amount of elapsed time from transmission of the images to the remote server 40 from the mobile electronic device 50 until transmission of the final index results is short; typically less than 10 seconds.

Figure 3A:
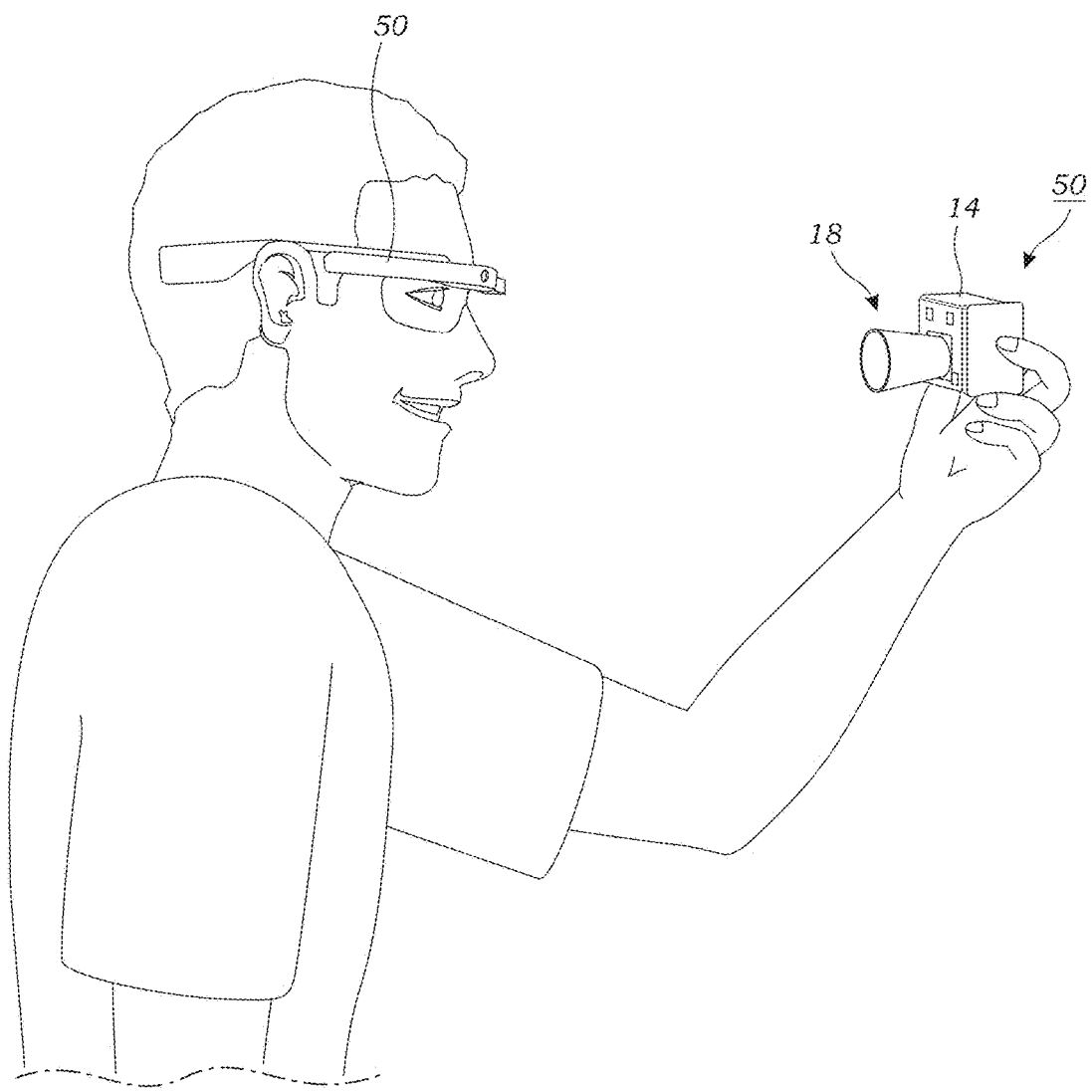
FIG. 3A illustrates a person holding the leaf-holding illuminator device with one hand and imaging the illuminated sample with a wearable mobile electronic device.
Figure 3B:
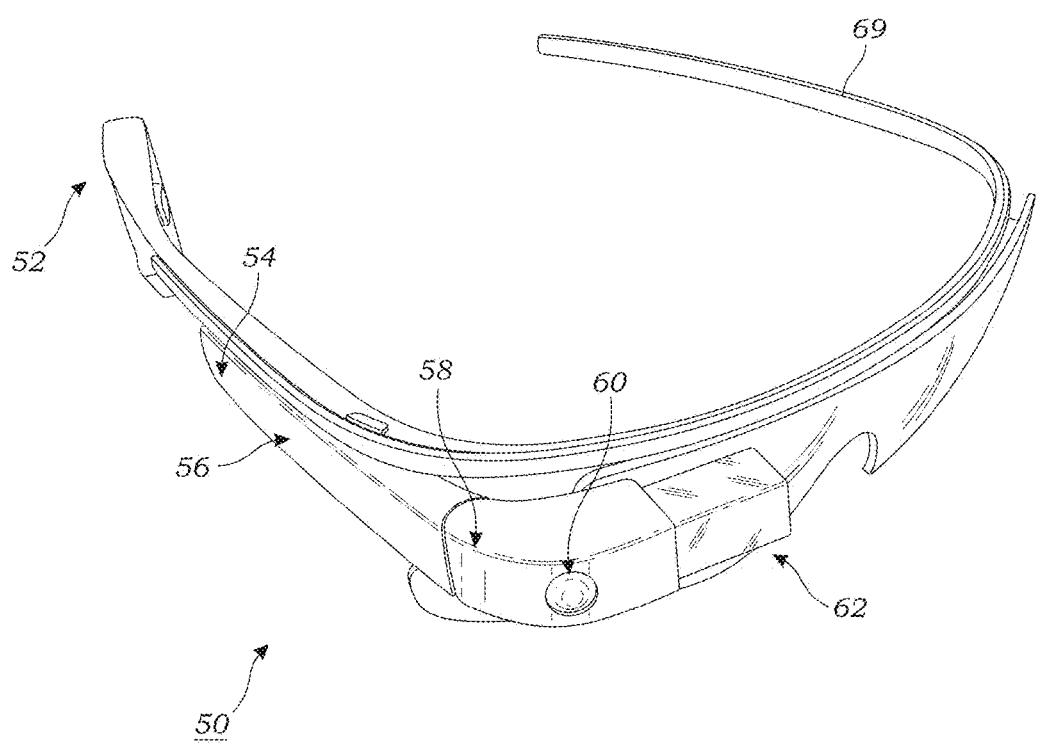
FIG. 3B illustrates the key components of the wearable mobile electronic device of FIG. 3A.

FIG. 3A illustrates one embodiment of how a user obtains images of the leaf 12 using the leaf-holding illuminator device 10 while wearing a wearable mobile electronic device 50 with camera functionality. In FIG. 3A, the user is wearing a glasses-based imaging device (i.e., Google Glass) which is illustrated in FIG. 3B that is running the application or program that is used to measure chlorophyll concentration. The wearable mobile electronic device 50 is in the shape and form of glasses that can be worn by the user. The wearable mobile electronic device 50 includes a battery 52, WiFi/Bluetooth transmitter/receiver 54, a touch-based interface 56, microphone 58, camera 58, and prism 60 all mounted on a glasses frame 69.

As seen in FIG. 3A, the user holds the leaf-holding illuminator device 10 (with leaf 12 loaded therein in one hand and is able to obtain the images using the Google Glass software interface. In another embodiment, a user may grip the leaf-holding illuminator device 10 in one hand while the other hand holds the mobile electronic device 50. For example, the mobile electronic device 50 may be a mobile phone and the user can align both devices; using one hand on the mobile electronic device 50 and the other hand holding the leaf-holding illuminator device 10. The user may take the picture, for example, by touching the screen or display with a finger or the like or sending a voice command.

Figure 3C:
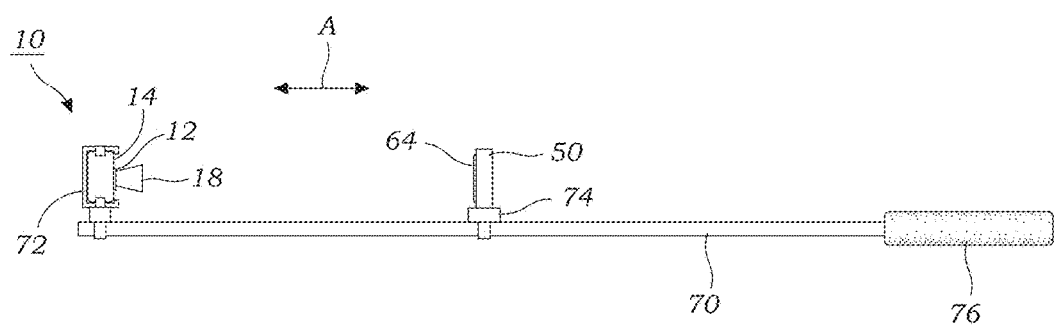
FIG. 3C illustrates an embodiment of a support base that is used to mount both the leaf-holding illuminator device and the mobile electronic device.

FIG. 3C illustrates another alternative method to obtain images of the leaf 12 using a mobile electronic device 50 such as a mobile phone or the like. In this embodiment, an extension member or common support base 70 such as a rod, pole, stick, tripod, or mount is used to mount both the leaf-holding illuminator device 10 and the mobile electronic device 50 to face one another wherein the camera 64 faces the aperture 36 of the leaf-holding illuminator device 10. In this example, the support base 70 is used much like a "selfie stick." For example, the support base 70 includes a first mount 72 that is used to hold the leaf-holding illuminator device 10 while the support base 70 includes a second mount 74 that is used to hold the mobile electronic device 50. In one aspect, the distance between the two mounts 72, 74 may be adjustable (as seen by arrow A in FIG. 3C) to enable the user to adjust to the ideal distance based on the focal length of the camera element in the mobile electronic device 50. The support base 70 may include a handle 76 or the like that can be used to grasped by the user to hold the support base 70 in the desired orientation. In addition, while FIG. 3C illustrates the leaf-holding illuminator device 10 in the mount 72 farthest from the handle 76 while the mobile electronic device 50 is in the mount 74 closest to the handle 76 it is possible to have the reverse configuration where the mobile electronic device 50 is located in the mount 72 with the leaf-holding illuminator device 10 in the mount 74 closes to the handle 76. Either configuration could be used.

Experimental Methods

The approach used in these experimental results to determine plant leaf chlorophyll concentration used Google Glass images of leaves by leveraging chlorophyll's low light absorption in the green part of the optical spectrum. The system used Google Glass as illustrated in FIG. 3B as the mobile electronic device 50, used with a custom developed software application for image capture, processing, and result display. The leaf-holding illuminator device 10 was designed as a handheld, 3D-printed leaf holder and illuminator unit which is used to enhance imaging contrast for various illumination conditions. As explained herein, the Google Glass device sends the captured images of the leaves of interest to a remote server for rapid processing and estimation of their chlorophyll content; subsequently, the server sends the results back to the originating Google Glass to be displayed to the user. The Google Glass application minimizes operator error using a simple gesture-based hands-free interface for easy positioning of the leaf illuminator unit. Of course, this is unique to the operating system of Google Glass and other user interfaces can be used.

In the experiments, the measured leaf chlorophyll content in was expressed in the form of SPAD indices. The SPAD index standard is used by the "gold" standard SPAD-502 chlorophyll meter and has both plant-independent and plant-specific mappings to chlorophyll concentration levels. To calibrate the tested platform for use under various ambient lighting conditions, each leaf was first measured using a SPAD-502 meter. The results of the calibration were used to map the intensity values calculated from Google Glass images to these SPAD indices.

Hardware

The hardware used in the system is includes the Google Glass as noted above and a custom-designed hand-held leaf-holding illuminator device as seen in FIGS. 1A and 1B. Note that experiments utilized only the built-in hardware of the Google Glass; no external hardware was attached to the Google Glass.

The leaf-holding illuminator device of FIGS. 1A and 1B was used to create uniform red and white LED illumination on the leaf sub-region to be measured. The entire leaf-holding illuminator device can be assembled under a cost of $30.00 USD even for low-volume manufacturing, and can be divided into three parts: the main body, external cap and internal electronic board. Both the main body and external cap were built using a 3D Fused Deposition Modeling (FDM) printer (Stratasys, Dimension Elite) that uses ABS plastic. The main body protects the electronics and forms a uniform light pattern internally. The external light isolation cap is added to reduce intensity changes on the internally illuminated leaf area due to external lighting conditions. This cap is attached onto the main body by using magnets placed on the main body and the inner part of the cap, enabling easy attachment and detachment for leaf placement between the cap and main body. The leaf can thus be placed into position without imparting any damage to the leaf by first removing the cap, then placing the leaf on the main body, and finally replacing the cap. The region of interest (ROI) this device can image on the leaf surface is approximately a circular area of 5 $cm^2$. An electronic board placed in the main body holds and can power two red 645 nm wavelength LEDs (Digikey #475-1322-1-ND) or two broad-band/white LEDs (Digikey #492-1180-ND). A switch allows the device to alternate between red and white illumination configurations; both sets of LEDs are never on at the same time. The illumination light from these LEDs is reflected off an aluminum foil attached to the body of the device (inside the cavity) and directly reflected towards the leaf ROI. A diffuser material is placed in between the reflected light and the leaf in order to generate a uniform pattern on the leaf surface. To achieve the necessary illumination levels for constant illumination under various exterior lighting conditions, the device is powered by three Alkaline AAA batteries placed in the upper part of the main body and power regulated using a voltage regulator.

Google Glass Application for Chlorophyll Measurements

After installing the Google Glass application for measuring chlorophyll, the user can run this app by either using the touch-pad on the side of Glass to select the application from the main menu or using the voice command interface with a spoken "OK Glass, image a leaf." Subsequently, the user will place the leaf of interest into the location designated in the accompanying device between the cap and the main body in preparation for imaging.

Once the application starts, the user is first prompted to select the ambient light option that best fits to the environment where leaf images will be taken. In this proof-of-concept application, this selection is limited to two general lighting environments, indoors or outdoors, which in the future could include more options to select from. After making this selection, the Google Glass application automatically shows a camera preview with a text message overlay requesting the user to take a picture of the leaf under red illumination. The user then turns on the red LEDs on the leaf-holding illuminator device and, to obtain the best repeatability in the measurement, the camera preview overlays a blue rectangular template for the user to match with the device profile. With this alignment, the relative distance and orientation between the leaf and the Google Glass camera 58 exhibit minimal variations. If fit to match the displayed template, the distance between the camera 58 and the leaf ROI is approximately 10 cm. Additionally, in order to ensure an optimal estimate of the chlorophyll levels, strong external light sources are prevented from pointing toward the leaf through the cap opening. This is done with proper orientation of the leaf-holding illuminator device.

After taking a picture of the leaf under red LED illumination, the Google Glass application opens the camera preview again, this time with a text message overlay that prompts the user to take an image of the same leaf under white LED illumination. The user switches the light source from red to white and takes an image of the leaf illuminated with white light. Having taken both of these images (red and white) for the same leaf of interest, the user can then upload them to a remote server using Google Glass's wireless connection (e.g., Wi-Fi), where they are digitally processed to create a chlorophyll concentration estimate. After processing the uploaded images, the calculated SPAD index is returned back to the originating Google Glass in the form of a timeline card, which displays an image of the ROI, the date and time of image capture, the validity of the ROI region, and the estimated SPAD index.

Remote Server-Based Leaf Image Processing

Due to the limited computational performance of Google Glass, a remote server is used to perform the post-processing of the data after image capture. All the Google Glass images are automatically compressed using the JPEG format, with each image generally not exceeding 1.2 MB in size. Once the leaf images are received, the server first validates each image using its ROI. To enforce the relative distance between the Glass and the leaf, the ROI is first digitally cropped using the template location and subsequently scanned for circular shapes with parameters corresponding to the physical dimensions of the circular cap of our leaf illuminator unit. Upon successful detection of the circular cap, the ROI was further limited by cropping it to a 110-pixel radius circular ROI, incorporating a 40-pixel margin to avoid border/edge effects and enhance the repeatability between experiments.

After successful detection of the illuminated leaf ROI, only the red channel information was extracted from the images taken under the red and white LED illumination. For each image the average (intensity level) of all the non-zero elements in the circularly masked leaf ROI is separately calculated. These two values are subsequently correlated to SPAD indices using calibration curves for different lighting conditions, where each calibration curve is generated by sampling several leaves from five different plant species (all selected from the UCLA Mildred E. Mathias Botanical Garden) covering a wide SPAD index range. To reduce variability caused by differing plant physiology and lighting conditions, the SPAD indices obtained from the red and white illumination images are then averaged to produce a final SPAD index for each leaf under test. This entire image processing step, leading to a quantified chlorophyll index, takes less than 10 sec on our server (CPU: Intel Core i5-760, RAM: 16 GB).

Results and Discussion

The digital calibration process of the Google Glass based platform to generate SPAD values for chlorophyll content was performed using five plant species (i.e., *Xylosma congestum, Vivurnum suspensum, Gingko biloba, Asparagus asparagoides*, and *Hypoestes artistata*) obtained from the UCLA Mildred E. Mathias Botanical Garden (see FIGS. 4A-4E). These plants were specifically chosen to have a wide variety of leaf sizes, internal structures, leaf thicknesses and most importantly, SPAD indices. In this calibration process, twenty leaves from each plant species were processed using the Google Glass device. As SPAD correlates better with chlorophyll for fully grown leaves, only used fully grown leaves from the branches of each plant were used. Due to the Google Glass camera's high sensitivity to lighting conditions, the system required a different calibration curve for indoor and outdoor conditions. It should be understood, however, that this not necessary should the light sensitivity not be an issue. In order to ensure high repeatability in measurements, all of the outdoor experiments were performed between 10 AM and 12 PM in a location shaded from direct sunlight exposure.

FIGS. 4A-4E show the two characteristic curves obtained for each one of our five calibration plant species, for indoor and outdoor lighting conditions. For each calibration curve, a total of twelve images for each leaf were taken (three images under red and white LED illumination, for indoor and outdoor lighting conditions), leading to a total of 240 Google Glass images per plant species. Since the leaf area used by the SPAD-502 instrument is ~6 $mm^2$, i.e., much smaller than the imaging area used in the leaf-holding illuminator device (~5 $cm^2$), the average of ten SPAD measurements taken using SPAD-502 for each leaf ROI was used to better calibrate the Google Glass based chlorophyll measurements. As shown in FIGS. 4A-4E, a strong correlation is obtained for each plant species between the average SPAD index measured using the commercially available SPAD-502 instrument and the average intensity of the red image channel measured using our Google Glass based chlorophyll measurement platform. The SPAD index variability, shown in FIGS. 4A-4E as standard deviation bars, refers to the variability of the ten measurements taken using the SPAD-502 instrument to cover the device's large imaging area (~5 cm$^2$) on the leaf. The Google Glass measurement standard deviations, however, represent the variability in the average intensity values of the three different images taken for each illumination condition and leaf ROI. Because of the significantly larger leaf area that Google Glass can image using the leaf-holding illuminator device, the Google Glass measurements show better repeatability as compared to the SPAD-502. Both indoor and outdoor results of the Google Glass measurements demonstrate a strong correlation to the SPAD-502 measurements. In general, the calibration results obtained for indoor imaging conditions provide better fit compared to the outdoor measurements, possibly due to a more stable and controlled lighting environment indoors.

Figure 5A:
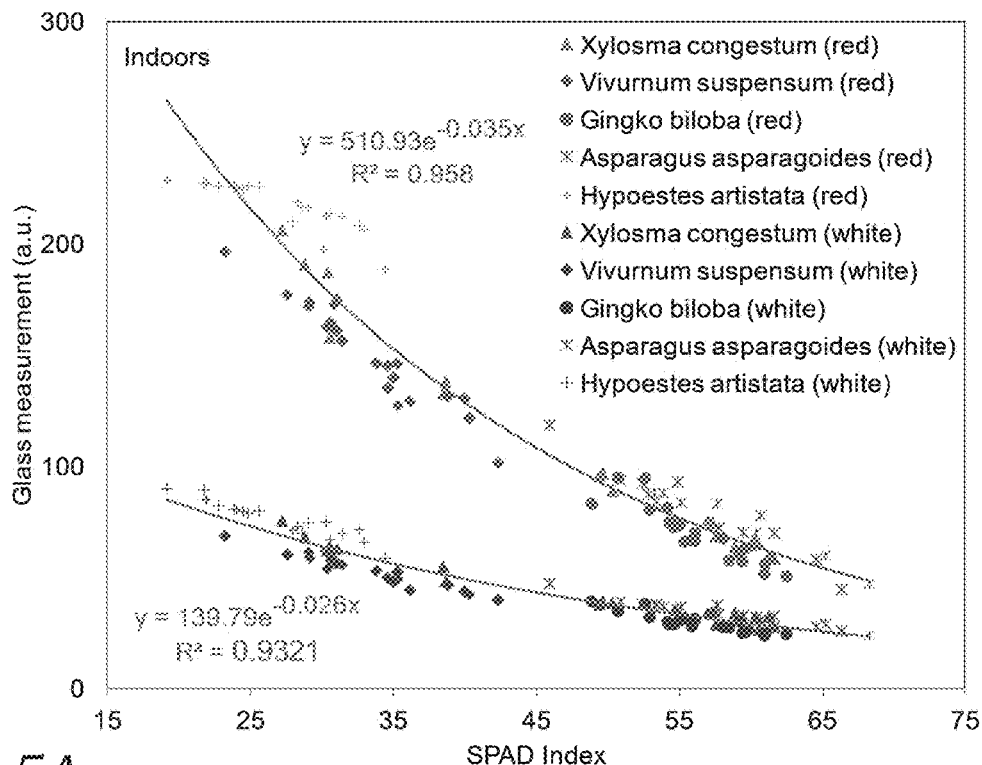
FIG. 5A illustrates the indoor calibration curves (upper graph is red illumination and lower graph is white illumination) for the glasses-based imaging device.
Figure 5B:
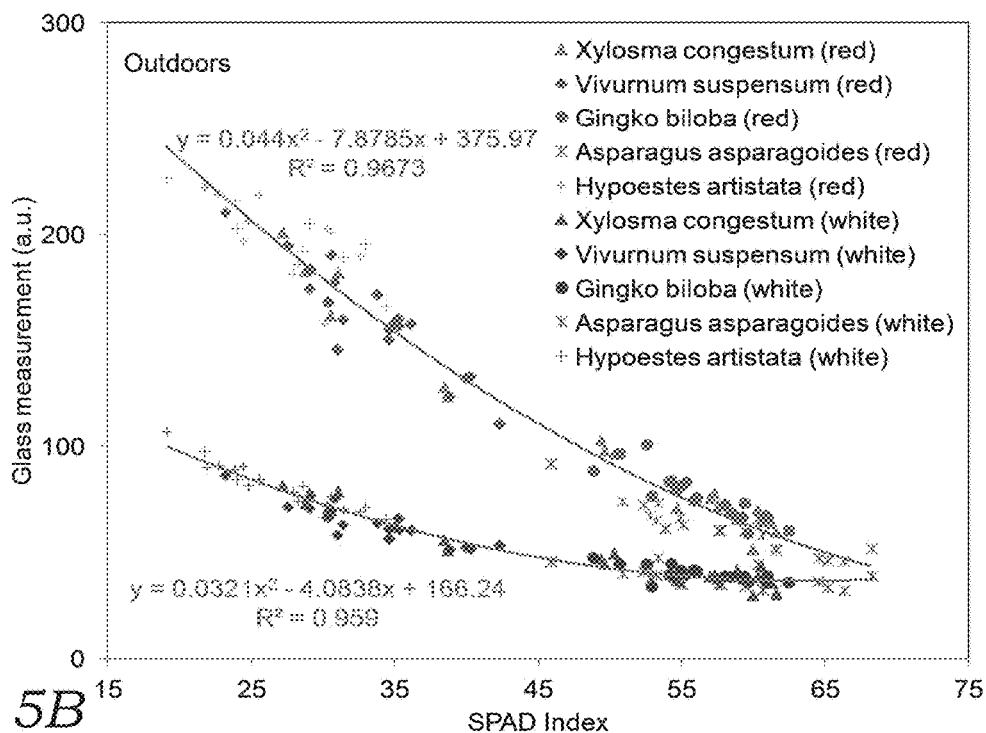
FIG. 5B illustrates the outdoor calibration curves (upper graph is red illumination and lower graph is white illumination) for the glasses-based imaging device.

The SPAD indices for these calibration plants shown in FIGS. 4A-4E cover a wide dynamic range. Next, this data was combined to generate plant-independent or generic calibration curves as shown in FIGS. 5A and 5B. To obtain these curves, one hundred individual leaves were used and twelve hundred pictures in total: three images of each leaf for both red and white LED illumination under indoor and outdoor lighting conditions. As FIGS. 5A and 5B illustrate, the Google Glass measurements provide a good correlation to the measurements made by the SPAD-502 instrument across a wide range of chlorophyll index values, ranging from 19.1 to 68.2. The calibration curves for red illumination (i.e., upper curve) and white illumination (i.e., lower curve) are shown for indoor and outdoor illumination conditions in FIGS. 5A and 5B, respectively. Optimizing curve fitting based off $R^2$ value resulted in exponential and quadratic calibration curves for indoor and outdoor illumination conditions irrespective of the choice of leaf illumination LED (red vs. white). In general, the red LED illumination data provided a better fit, but were also sparser than the white LED illumination data. Note also that although the indoor test results generated more accurate plant-specific calibration curves (FIGS. 4A-4E), for our plant-independent calibration curves the outdoor curves exhibit slightly superior fit, most likely due to the poor fit of the *Hypoestes artistata* for indoor conditions.

Figure 6A:
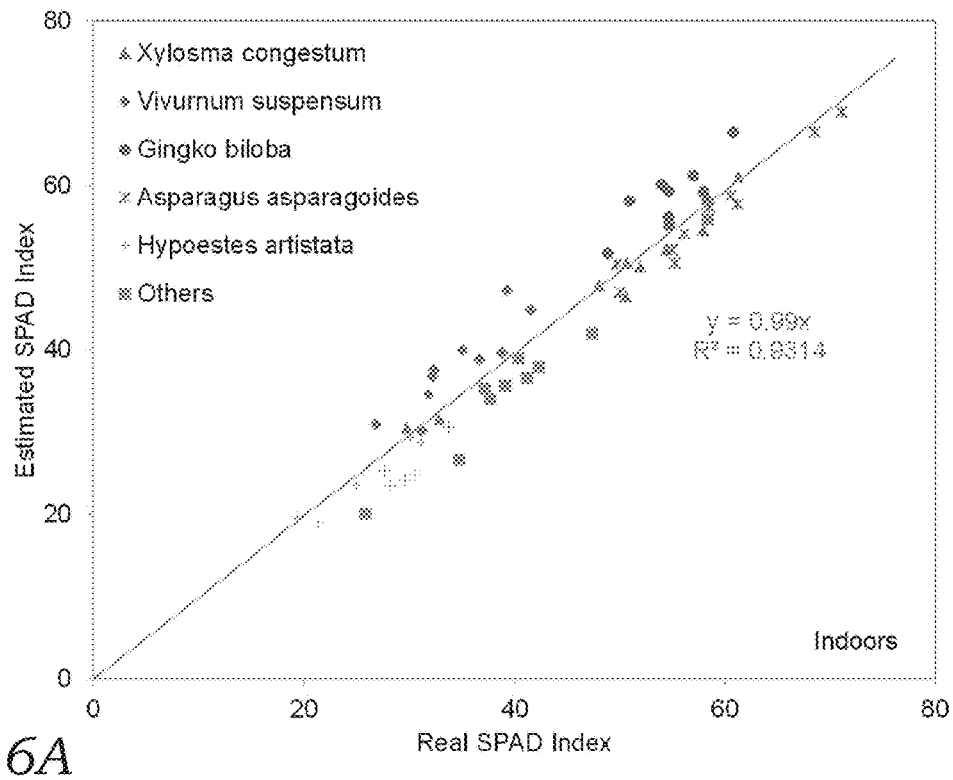
FIG. 6A illustrates the blind test results (indoor measurements) of the glasses-based imaging device showing the estimated SPAD index values as a function of the real or actual SPAD index value.
Figure 6B:
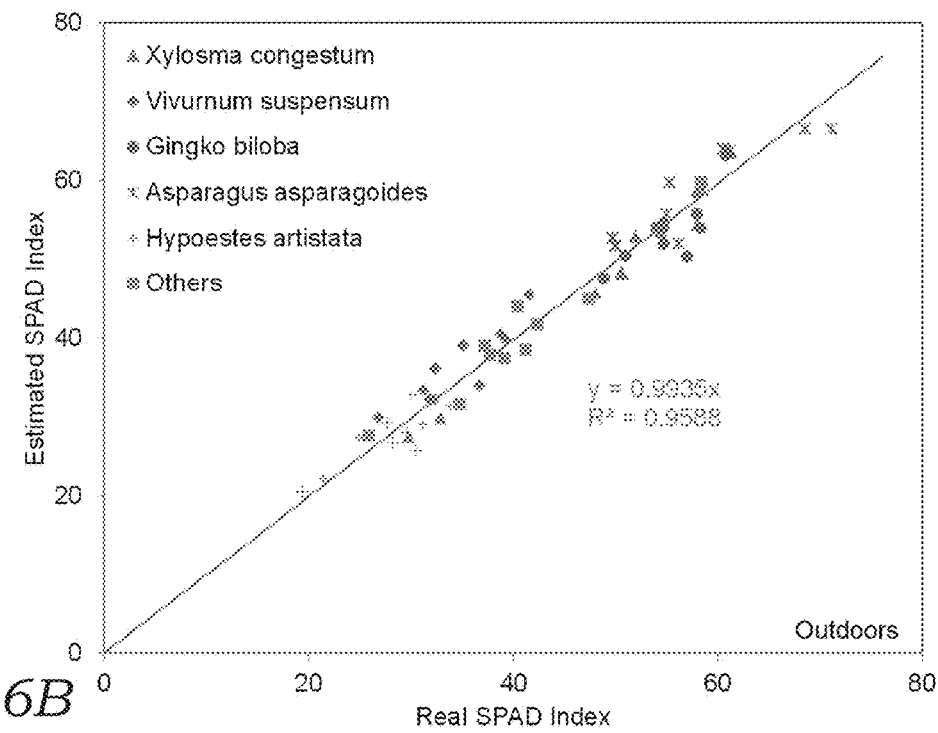
FIG. 6B illustrates the blind test results (outdoor measurements) of the glasses-based imaging device showing the estimated SPAD index values as a function of the real or actual SPAD index value.

After this calibration step, tested the performance of the Google Glass based chlorophyll quantification system was tested by performing blind tests with sixty fresh leaves taken from fifteen (15) different species, where fifty of them were leaves from the same five (5) species used in the calibration process and the remaining ten (10) were leaves taken from ten (10) other species (*Baphia racemosa, Crolalaria agatiflora, Justicia leonardii, Alstonia venenata, Tristaniopsis laurina, Drypetes australasia, Melicytus ramiflorus* (male), *Montanoa guatemalensis, Tithonia diversifolia, Ceratozamia hildae*) that were randomly chosen from the UCLA Mildred E. Mathias Botanical Garden. Each leaf was tested three times by taking images in red and white illumination configurations, as described previously. The Google Glass based blind measurement results are shown in FIGS. 6A and 6B, where the platform achieved a good correlation to the blind measurements made by a SPAD-502 chlorophyll reader.

In the blind tests, for the same five (5) plant species that were used in the calibration process, a mean SPAD index error of 2.8 and 2.2 was obtained with standard deviations of 1.96 and 1.46, for indoor and outdoor lighting conditions, respectively. If all fifteen (15) species were to be included, the platform achieved a mean error of 3.0 and 2.2 with standard deviations of 2.01 and 1.40, for indoor and outdoor conditions, respectively. These numbers indicate that the platform's outdoor tests have slightly superior performance, as also predicted by the better calibration curve fit for the outdoor case compared to the indoor lighting conditions (see FIGS. 5A and 5B). Additionally, the high correlation to the measurements of SPAD-502 reader is maintained for randomly selected plant species not used in our calibration process, achieving similar accuracies when compared with the plant species that were included in our calibration experiments. The fact that the calibration performs very well with other plant species suggests that the selection of calibration plants is diverse enough for accurate measurement of the chlorophyll content in various plants.

The wireless connectivity requirement of the chlorophyll measurement platform described herein does not pose a limitation for this technique. The total number of wireless internet users reached 2.1 billion in 2013, and this growth is not limited only to developed countries. In fact, the mobile-broadband subscriptions in developing countries increased from 472 million to 1.16 billion between 2011 and 2013. Additionally, there are fast-paced projects (e.g., Google's Project Loon) that aim to widely deliver wireless connectivity to remote and rural parts of the world. Considering the widespread growth of wireless connectivity over the past decade and the new projects bringing remote and rural parts of the world online, the chlorophyll measurement platform described herein is very well suited for today's highly connected digital world.

One additional advantage of this platform is that the custom designed application can also provide GPS (Global Positioning System) information of chlorophyll measurements, which is important for spatio-temporal mapping, tracking and analysis of the results. The same feature also permits the users to continue their chlorophyll measurements without stopping or waiting for a local result since they can later correlate their tests with the GPS coordinates on a map and thus be able to exactly determine where each test was captured, at what time, etc. Furthermore, since it is an imaging-based design, the Google Glass chlorophyll measurement system can also be used to determine leaf skeletal structure information in addition to chlorophyll concentration. Finally, based on the correlation between the SPAD index value and the nitrogen content of the plant, the Google Glass based platform can also be used to indirectly monitor the soil nutrition content and the crop growth process.

The custom-designed Android-based application together with a 3D-printed hand-held leaf-holding illuminator device can rapidly, accurately and non-destructively estimate chlorophyll levels in various plant species over a wide range of chlorophyll concentrations. Measurements and SPAD estimations successfully exploit chlorophyll's characteristic spectral signature by utilizing the red channel intensity of captured images as the main indicator for chlorophyll concentration. Using this methodology, plant-independent calibration curves were successfully generated, accurately mapping the captured images of plant leaves to standard SPAD indices. The results suggest that this method can be extended to a wider SPAD range by including plants with higher and lower SPAD indices. This platform can be used as a chlorophyll concentration measurement tool for quick and accurate assessment of plant health under different lighting conditions, providing a good alternative to existing devices that are more complex, expensive, and use more time consuming methods.

While embodiments of the present invention have been shown and described, various modifications may be made without departing from the scope of the present invention.

The invention, therefore, should not be limited, except to the following claims, and their equivalents.

What is claimed is:

1. A system for measuring chlorophyll concentration in a leaf sample comprising:
   a leaf-holding illuminator device comprising a main body containing a power source, a plurality of switchable light sources emitting light at different spectra, a diffuser interposed within an optical path formed between the plurality of switchable light sources and the leaf, and a cap having an aperture therein that is detachably secured to the main body, wherein the leaf sample is interposed between the main body and the cap; and
   a mobile electronic device having a camera configured to capture images of the leaf illuminated by the plurality of switchable light sources, the mobile electronic device having wireless connectivity to a network and an application stored therein configured to transfer the images to a remote computer via the network.

2. The system of claim 1, wherein the mobile electronic device comprises a wearable imaging device.

3. The system of claim 2, wherein the mobile electronic device comprises a glasses-based imaging device.

4. The system of claim 1, wherein the mobile electronic device comprises one of a mobile phone, tablet, and webcam.

5. The system of claim 1, wherein the mobile electronic device captures images of transmitted light through the leaf.

6. The system of claim 1, wherein the mobile electronic device captures images of reflected light from the leaf.

7. The system of claim 1, wherein the plurality of switchable light sources comprises a red light source and a broadband light source.

8. The system of claim 1, wherein the cap comprises a base connected to an extension.

9. The system of claim 1, wherein at least one of the cap and main body has fastening means for detachably securing the cap to the main body.

10. A method of measuring chlorophyll concentration in a leaf sample comprising:
    loading the leaf sample into a leaf-holding illuminator device;
    illuminating the leaf sample with a leaf-holding illuminator device at a first illumination spectrum with a first illumination source and a second illumination spectrum with a second illumination source;
    capturing images of the illuminated leaf sample with a camera of a mobile electronic device while being illuminated at the first illumination spectrum and the second illumination spectrum;
    the mobile electronic device transferring the captured images at the first illumination spectrum and the second illumination spectrum to a remote server;
    the remote server extracting a region of interest (ROI) from each of the transferred images and computing an average intensity value for the ROI obtained by the first illumination source and an average intensity value for the ROI obtained by the second illumination source;
    the remote server generating a chlorophyll index value for the first illumination source based on a comparison of the average intensity value for ROI obtained by the first illumination source with a calibration curve;
    the remote server generating a chlorophyll index value for the second illumination source based on a comparison of the average intensity value for ROI obtained by the second illumination source with a calibration curve;
    the remote server calculating a final chlorophyll index value based on a function applied to the chlorophyll index value for the first illumination source and the chlorophyll index value for the second illumination source; and
    transferring the final chlorophyll index value from the remote server to the mobile electronic device.

11. The method of claim 10, wherein the mobile electronic device comprises a glasses-based imaging device.

12. The method of claim 10, wherein the remote server calculates the final chlorophyll index value based on an average of the chlorophyll index value for the first illumination source and the chlorophyll index value for the second illumination source.

13. The method of claim 10, wherein the captured images of the illuminated leaf sample comprises transmitted light.

14. The method of claim 10, wherein the captured images of the illuminated leaf sample comprises reflected light.

15. The method of claim 10, wherein the first illumination source emits red light and the second illumination source emits a broadband spectrum of light.

16. The method of claim 10, wherein the chlorophyll index value comprises a chlorophyll content index (CCI).

17. The method of claim 10, wherein a dedicated application executed on the mobile electronic device transmits the captured images at the first illumination spectrum and the second illumination spectrum to the remote server and receives the final chlorophyll index value.

18. The method of claim 10, wherein the leaf-holding illuminator device is held by a person with a first hand and a second hand of the person holds the mobile electronic device during the image capturing operation.

19. The method of claim 10, wherein the leaf-holding illuminator device and the mobile electronic device are mounted on a support base.

20. A method of measuring chlorophyll concentration in a leaf sample comprising;
    loading the leaf sample into a leaf-holding illuminator device;
    illuminating the leaf sample with a leaf-holding illuminator device at a first illumination spectrum with a first illumination source and a second illumination spectrum with a second illumination source;
    capturing images of the illuminated leaf sample with a camera of a mobile electronic device while being illuminated at the first illumination spectrum and the second illumination spectrum;
    the mobile electronic device transferring the captured images at the first illumination spectrum and the second illumination spectrum to a remote server;
    the remote server extracting a region of interest (ROI) from each of the transferred images and computing an average intensity value for the ROI obtained by the first illumination source and an average intensity value for the ROI obtained by the second illumination source;
    the remote server generating a chlorophyll index value for the first illumination source based on a comparison of the average intensity value for ROI obtained by the first illumination source with a calibration curve;
    the remote server generating a chlorophyll index value for the second illumination source based on a comparison of the average intensity value for ROI obtained by the second illumination source with a calibration curve;
    the remote server transferring the chlorophyll index value for the first illumination source and the chlorophyll index value for the second illumination source to the mobile electronic device;

the mobile electronic device calculating a final chlorophyll index value based on the chlorophyll index value for the first illumination source and the chlorophyll index value for the second illumination source.

\* \* \* \* \*